US012752104B2

(12) United States Patent
Van den Heuvel et al.

(10) Patent No.: US 12,752,104 B2
(45) Date of Patent: Oct. 6, 2026

(54) WIRELESSLY POWERED MEDICAL IMPLANT FOR TREATMENT OF SLEEP-DISORDERED BREATHING

(71) Applicant: Cochlear Limited, Macquarie University (AU)

(72) Inventors: Koen Erik Van den Heuvel, Hove (BE); Catherine Picard, St. Aubin (FR); Werner Meskens, Opwijk (BE)

(73) Assignee: Cochlear Limited, Macquarie University (AU)

( * ) Notice: Subject to any disclaimer, the term of this patent is extended or adjusted under 35 U.S.C. 154(b) by 309 days.

(21) Appl. No.: 18/291,886

(22) PCT Filed: Aug. 8, 2022

(86) PCT No.: PCT/IB2022/057380

§ 371 (c)(1),
(2) Date: Jan. 24, 2024

(87) PCT Pub. No.: WO2023/026124

PCT Pub. Date: Mar. 2, 2023

(65) Prior Publication Data

US 2025/0082927 A1 Mar. 13, 2025

Related U.S. Application Data

(60) Provisional application No. 63/236,489, filed on Aug. 24, 2021.

(51) Int. Cl.
*A61N 1/00* (2006.01)
*A61N 1/05* (2006.01)
(Continued)

(52) U.S. Cl.
CPC ......... *A61N 1/0556* (2013.01); *A61N 1/0548* (2013.01); *A61N 1/36146* (2013.01); *A61N 1/3787* (2013.01)

(58) Field of Classification Search
CPC ................ A61N 1/0556; A61N 1/0548; A61N 1/36146; A61N 1/3787; A61N 1/0551; A61N 1/3601; A61N 1/3611
See application file for complete search history.

(56) References Cited

U.S. PATENT DOCUMENTS 8,892,205 B2 11/2014 Miiller, III et al.
9,415,215 B2 8/2016 Mashiach
(Continued)

FOREIGN PATENT DOCUMENTS

JP 2019/503722 2/2019
KR 10-2020-0091279 7/2020

OTHER PUBLICATIONS

Search Report and Written Opinion received in International Application No. PCT/IB2022/057380, dated Nov. 18, 2022.

*Primary Examiner* — Scott M. Getzow
(74) *Attorney, Agent, or Firm* — Knobbe, Martens, Olson & Bear, LLP

(57) ABSTRACT

An apparatus includes first circuitry configured to be implanted on or within a recipient's body and to apply stimulation signals to at least one muscle of a recipient and/or to at least one neuron configured to control the at least one muscle. The apparatus further includes second circuitry configured to be implanted on or within the recipient's body and configured to wirelessly receive electrical power from a power source external to the recipient's body and to provide at least a portion of the received electrical power to the first circuitry. The second circuitry includes a plurality of coils, each coil of the plurality of coils having at least one electrically conductive conduit encircling a center axis of the coil. The coils are configured to be implanted on or within the recipient's body with different orientations and/or positions relative to one another.

18 Claims, 8 Drawing Sheets

(51) Int. Cl.
*A61N 1/36* (2006.01)
*A61N 1/378* (2006.01)

(56) References Cited

U.S. PATENT DOCUMENTS

| | | | | |
|---|---|---|---|---|
| 9,943,686 | B2 | 4/2018 | Mashiach | |
| 10,617,880 | B2 | 4/2020 | Zellmer et al. | |
| 2002/0049479 | A1* | 4/2002 | Pitts ..................... | A61N 1/3601 607/42 |
| 2008/0103407 | A1 | 5/2008 | Bolea et al. | |
| 2013/0261693 | A1* | 10/2013 | Gross ................... | A61N 1/0526 607/42 |
| 2020/0324127 | A1 | 10/2020 | Leigh | |
| 2021/0121706 | A1* | 4/2021 | Deininger ............ | A61N 1/3787 |

* cited by examiner

WIRELESSLY POWERED MEDICAL IMPLANT FOR TREATMENT OF SLEEP-DISORDERED BREATHING

BACKGROUND

Field

The present application relates generally to systems and methods for treating sleep-disordered breathing (SDB) conditions, and more specifically, for wirelessly providing power to a medical implant for preventing or minimizing SDB events using stimulation signals.

Description of the Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect disclosed herein, an apparatus comprises first circuitry configured to be implanted on or within a recipient's body. The first circuitry is configured to apply stimulation signals to at least one muscle of a recipient and/or to at least one neuron configured to control the at least one muscle. The apparatus further comprises second circuitry configured to be implanted on or within the recipient's body. The second circuitry is configured to wirelessly receive electrical power from a power source external to the recipient's body and to provide at least a portion of the received electrical power to the first circuitry. The second circuitry comprises a plurality of coils, each coil of the plurality of coils comprising at least one electrically conductive conduit encircling a center axis of the coil. The coils are configured to be implanted on or within the recipient's body with different orientations and/or positions relative to one another.

In another aspect disclosed herein, a method comprises receiving a time-varying magnetic flux using at least one coil of a plurality of coils implanted on or within a recipient's body. The coils have different orientations and/or positions relative to one another. The method further comprises generating electrical power using the received time-varying magnetic flux. The method further comprises generating stimulation signals using at least some of the electrical power. The method further comprises applying the stimulation signals to at least one muscle of the recipient's body and/or to at least one neuron configured to control the at least one muscle.

In another aspect disclosed herein, an apparatus comprises at least one implantable electrode configured to apply stimulation signals to at least one muscle of a recipient and/or to at least one neuron configured to control the at least one muscle. The apparatus further comprises a plurality of implantable RF coils having different orientations and/or positions relative to one another, the plurality of implantable RF coils configured to wirelessly receive electrical power from an external power source. The apparatus further comprises processor circuitry configured to provide at least a portion of the electrical power received by the plurality of implantable RF coils to the at least one implantable electrode.

BRIEF DESCRIPTION OF THE DRAWINGS

Implementations are described herein in conjunction with the accompanying drawings, in which.

DETAILED DESCRIPTION

Figure 1A:
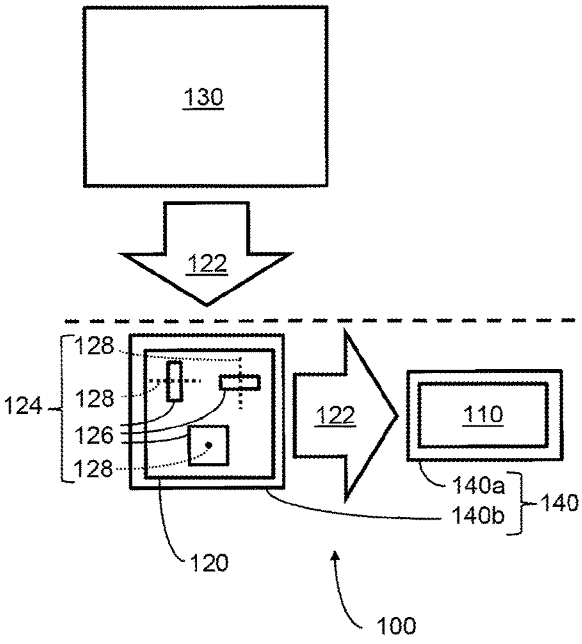
FIGS. 1A-ID schematically illustrate various example apparatus in accordance with certain implementations described herein.

Certain implementations described herein provide a sleep apnea treatment system comprising a stimulator implant configured to stimulate a portion of the recipient's tongue or hypoglossal nerve to inhibit sleep apnea. The stimulator implant is wirelessly powered during a sleep session by an external device (e.g., a pillow charger on which a recipient rests their head). The stimulator implant comprises a plurality of RF coils having different locations and/or orientations relative to each other so as to maintain efficient wireless power transfer to the implanted RF coils from RF coils of the external device, even when the recipient's head is moved relative to the external device during the sleep session (e.g., when the recipient turns over in bed).

The teachings detailed herein are applicable, in at least some implementations, to any type of implantable medical device (e.g., implantable stimulation system) comprising a first portion implanted on or within the recipient's body and configured to provide stimulation signals to a portion of the recipient's body and a second portion (e.g., implanted on or within the recipient) configured to wirelessly receive power from a power source external to the recipient's body and to provide power to the first portion. For example, the implantable medical device can comprise a neurostimulation system and/or a muscle stimulation system. Implementations can include any type of medical device that can utilize the teachings detailed herein and/or variations thereof.

Merely for ease of description, apparatus and methods disclosed herein are primarily described with reference to an illustrative medical device, namely an implantable stimulation system configured to treat sleep-disordered breathing (SDB) conditions, for example, obstructive sleep apnea (OSA) conditions. However, the teachings detailed herein and/or variations thereof may also be used with a variety of other medical devices that provide a wide range of therapeutic benefits to recipients, patients, or other users. In some implementations, the teachings detailed herein and/or variations thereof can be utilized in other types of implantable medical devices beyond those configured to treat sleep-related conditions. For example, apparatus and methods disclosed herein and/or variations thereof may also be used with one or more of the following: vestibular devices (e.g., vestibular implants); sensory prostheses; auditory devices (e.g., bionic ears); auditory prostheses (e.g., cochlear implants); visual devices (e.g., bionic eyes); visual prostheses (e.g., retinal implants); sensors (e.g., electroencephalogram sensors); cardiac pacemakers; drug delivery systems; defibrillators; functional electrical stimulation devices; catheters; brain implants; seizure devices (e.g., devices for monitoring and/or treating epileptic events); devices to treat migraine headaches, depression, tinnitus, or taste disfunction; electroporation; muscle stimulation devices; pain relief devices; swallowing treatment devices (e.g., devices for treating difficulties with the hyoglossus and/or thyrohyoid muscles); dysphagia treatment devices; devices for treating dry mouth (e.g., xerostomia or hyposalivation), devices for treating excessive or absence of muscle movement due to stroke, Parkinson's disease, or other brain disorders, devices for treating hypertension (e.g., by stimulating the carotid sinus barosensory system); devices for treating the spine, back pain, foot drop; etc.

Obstructive sleep apnea (OSA), an example of a sleep-disordered breathing (SDB) disorder, is a widespread problem affecting adults in which a person's breathing airways are obstructed during sleep due to loss of tonus of the musculature surrounding the upper airways which results in tissues, either partially or completely, blocking the airways. Such blockage can alter or even stop the person's breathing (e.g., for 20-40 seconds or longer), resulting in snoring, hypoxemia, and/or hypoxia. The discomfort resulting from the stoppage of breathing can partially or fully arouse the person from sleep, upon which the tonus of the surrounding musculature increases, thereby reducing the blockage of the airways by the tissues and allowing the person to resume breathing and to return to sleep. This cycle typically repeats itself throughout the night, sometimes without the person realizing it, and the resultant inadequate sleep can be severe (e.g., disease progression; day-to-day quality of life of the individual; cost to society), leading to poorer quality of life, memory dysfunction, and a higher prevalence of developing or quickening the progression of other diseases.

FIGS. 1A-ID schematically illustrate various example apparatus 100 in accordance with certain implementations described herein. The apparatus 100 comprises first circuitry 110 (e.g., stimulation circuitry; stimulation device) configured to be positioned (e.g., implanted) on or within a recipient's body and configured to apply stimulation signals 112 to at least one muscle of a recipient and/or to at least one neuron configured to control the at least one muscle. The apparatus 100 further comprises second circuitry 120 (e.g., power receiving circuitry) configured to be implanted on or within the recipient's body. The second circuitry 120 is configured to wirelessly receive electrical power 122 from a power source 130 external to the recipient's body and to provide at least a portion 123 of the received electrical power 122 to the first circuitry. The second circuitry 120 comprises a plurality of coils 124, each coil 124 of the plurality of coils 124 comprising at least one electrically conductive conduit 126 encircling a center axis 128 of the coil 124. The coils 124 are configured to be implanted on or within the recipient's body with different orientations and/or positions relative to one another.

Figure 1B:
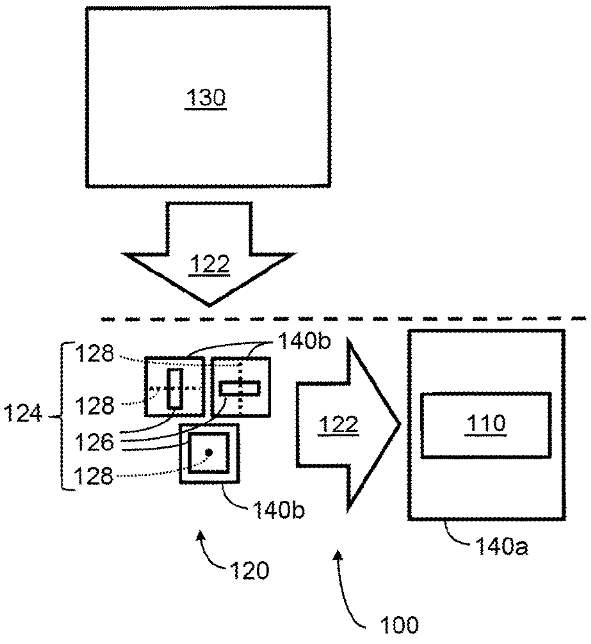
FIG. 1E schematically illustrates a sagittal plane view of a portion of a recipient's skull and tissue with a portion of the first circuitry in accordance with certain implementations described herein.

In certain implementations, the apparatus 100 further comprises at least one housing 140 containing (e.g., hermetically sealing within) at least one of the first circuitry 110 and the second circuitry 120. The at least one housing 140 can comprise at least one biocompatible material (e.g., polymer; PEEK: silicone; titanium; titanium alloy; ceramic). As schematically illustrated in FIGS. 1A-1B, the at least one housing 140 can comprise a first housing 140*a* containing at least a portion of the first circuitry 110 and at least one second housing 140*b* containing at least a portion of the second circuitry 120. The first and second housings 140*a,b* can be configured to be implanted on or within the recipient's body (e.g., subcutaneously, denoted in FIGS. 1A-1B as being below the dashed line). The first and second housings 140*a,b* can be integral with one another (e.g., portions of a common housing) or can be separate from one another (e.g., as schematically illustrated in FIGS. 1A-1B). As described herein and as schematically illustrated in FIG. 1B, the second housing 140*b* can comprise a plurality of sub-housings, each sub-housing containing (e.g., hermetically sealing within) at least one corresponding coil 124 of the plurality of coils 124.

Figure 1C:
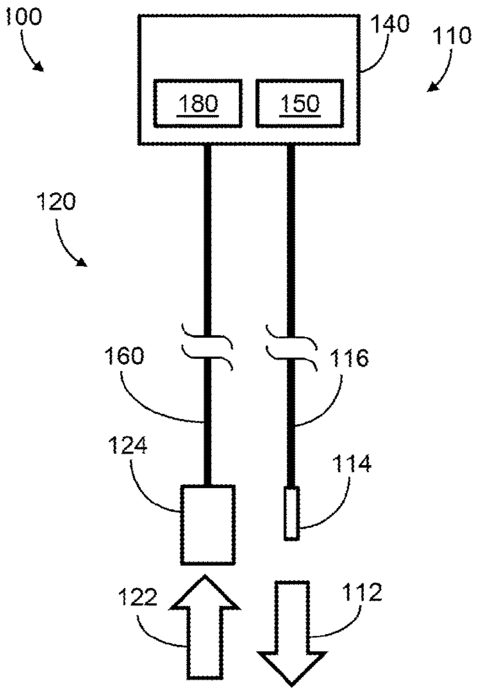
Figure 1D:
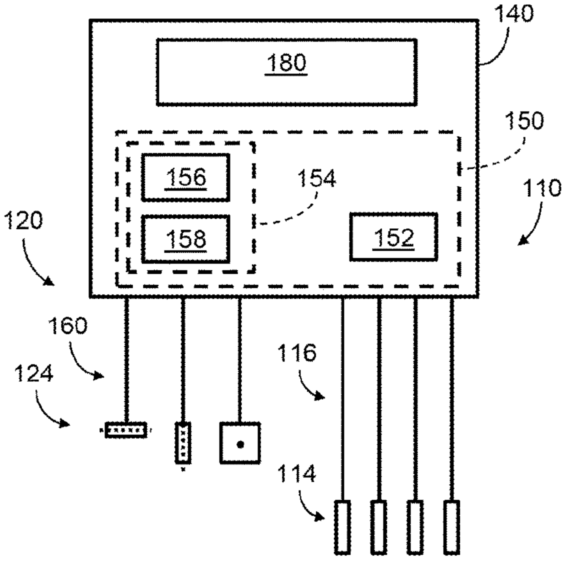

In certain implementations, as schematically illustrated by FIGS. 1C-ID, the first circuitry 110 comprises at least one stimulation element 114 (e.g., electrical electrode; electrical contact; optical emitter; optical contact) configured to be positioned (e.g., implanted) on or within the recipient's body and to apply stimulation signals 112 to at least one muscle of the tongue of the recipient and/or to a portion of a hypoglossal nerve of the recipient (e.g., during a sleep session of the recipient). In certain implementations, as schematically illustrated by FIG. 1D, the first circuitry 110 comprises a plurality of stimulation elements 114 positioned relative to one another such that the plurality of stimulation elements 114 can be selectively activated to apply different stimulations signals 112 to the at least one muscle and/or to the at least one neuron. For example, the plurality of stimulation elements 114 can comprise two or more electrodes and the first circuitry 110 can be configured to apply selected voltage differences between selected pairs of the two or more electrodes (e.g., different stimulation vectors).

For example, the at least one stimulation element 114 can comprise at least one cuff electrode surrounding a portion (e.g., nerve branch) of a hypoglossal nerve of the recipient and/or at least one surface electrode in proximity to a portion (e.g., nerve branch) of the hypoglossal nerve of the recipient, and can be configured to apply an electrical voltage and/or current to the portion of the hypoglossal nerve. Other types of stimulation elements 114 are also compatible with certain implementations described herein, including, but not limited to, epineurial electrodes, circumneural electrodes, interfascicular electrodes, intraneural electrodes, regenerative electrodes, and other electrodes compatible with functional electrical stimulation.

In certain implementations, the first circuitry 110 has a proximal end connected to a housing 140, and a distal end comprising the at least one stimulation element 114. For example, as schematically illustrated by FIGS. 1C-1D, the first circuitry 110 can comprise at least one signal conduit 116 (e.g., wire; cable) configured to transmit stimulation control signals from control circuitry 150 within the housing 140 to the at least one stimulation element 114. In certain other implementations, the at least one signal conduit 116 is absent and the stimulation control signals are wirelessly transmitted from the control circuitry 150 to the at least one stimulation element 114 (e.g., transmitted by radio frequency signals from an antenna of the control circuitry 150 to an antenna of the stimulation element 114). In certain implementations, the at least one stimulation element 114 and the second circuitry 120 are both on and/or within (e.g., integrated with) the same housing 140 and are in proximity to the portion of the tongue and/or hypoglossal nerve that is to receive the stimulation signals 112.

Figure 1E:
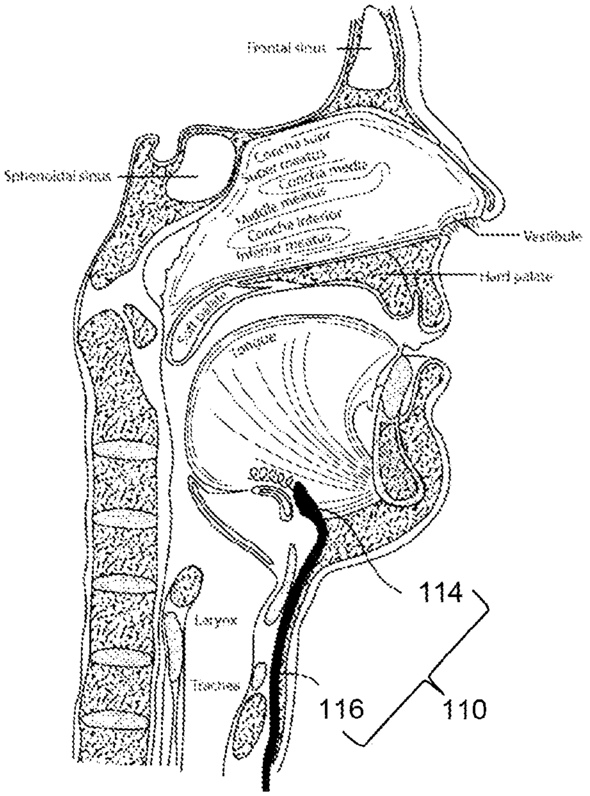

FIG. 1E schematically illustrates a sagittal plane view of a portion of a recipient's skull and tissue with a portion of the first circuitry 110 in accordance with certain implementations described herein. The first circuitry 110 of FIG. 1E comprises a muscle stimulation device (see, e.g., U.S. Pat. No. 8,892,205) in which the at least one stimulation element 114 is implanted within the recipient's tongue and is configured to apply the stimulation signals 112 (e.g., electrical stimulation signals; optical stimulation signals) to at least one muscle of the recipient's tongue. In certain other implementations, the first circuitry 110 comprises a neuromodulation device (e.g., a hypoglossal nerve stimulation device, see, e.g., U.S. Pat. Nos. 9,415,215 and 9,943,686) in which the at least one stimulation element 114 is configured to apply the stimulation signals 112 to a portion of the hypoglossal nerve.

In certain implementations, as schematically illustrated by FIGS. 1C-ID, the second circuitry 120 comprises at least one signal conduit 160 (e.g., wire; cable) configured to transmit at least a portion 123 of the received power 122 from the plurality of coils 124 to other portions of the apparatus 100 (e.g., the first circuitry 110; the control circuitry 150). The second circuitry 120 comprises a plurality of coils 124 (e.g., implantable RF coils) having different orientations and/or positions relative to one another and configured to wirelessly receive electrical power from the external power source 130. For example, each coil 124 of the plurality of coils 124 can comprise at least one electrically conductive conduit 126 encircling a center axis 128 of the coil 124. In certain implementations, each coil 124 of the plurality of coils 124 comprises multiple (e.g., 2, 3, 4, 5, or more) turns or loops of the electrically conductive conduit 126 (e.g., electrically insulated single-strand or multi-strand platinum or gold wire) and is configured to be wirelessly coupled to the power source 130 so as to form a transcutaneous energy transfer link configured to wirelessly transmit power from the power source 130 external to the recipient's body to at least one coil 124 of the second circuitry 120.

Figure 2A:
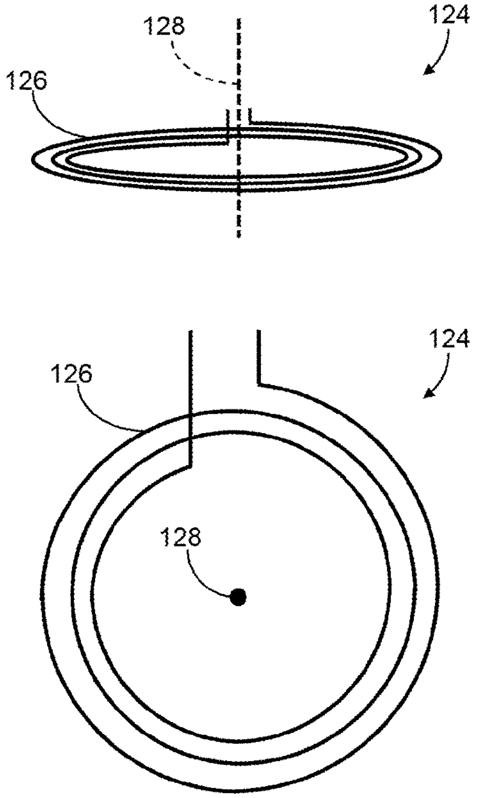
FIG. 2A schematically illustrates a perspective view and a top view of an example coil in accordance with certain implementations described herein.

FIG. 2A schematically illustrates a perspective view and a top view of an example coil 124 in accordance with certain implementations described herein. The example coil 124 of FIG. 2A comprises an electrically conductive conduit 126 that is substantially planar and is substantially perpendicular to a center axis 128 of the coil 124. The example coil 124 of FIG. 2A has three turns or loops encircling the center axis 128, although other numbers of turns or loops are also compatible with certain implementations described herein. An example width (e.g., diameter) of the coil 124 of FIG. 2A can be in the range of 10 millimeters to 35 millimeters (e.g., 20 millimeters) in the plane substantially perpendicular to the center axis 128.

Figure 2B:
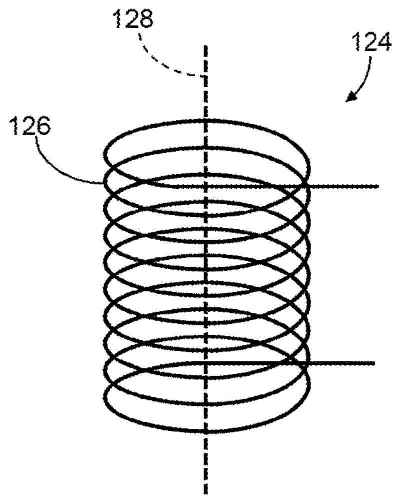
FIG. 2B schematically illustrates a perspective view of another example coil in accordance with certain implementations described herein.

FIG. 2B schematically illustrates a perspective view of another example coil 124 in accordance with certain implementations described herein. The example coil 124 of FIG. 2B comprises an electrically conductive conduit 126 that is substantially cylindrical with a longitudinal axis that is parallel to and/or coincident with the center axis 128 of the coil 124. The example coil 124 of FIG. 2B has nine turns or loops encircling the center axis 128, although other numbers of turns or loops are also compatible with certain implementations described herein. An example length of the coil 124 of FIG. 2B along the longitudinal axis can be in the range of 5 millimeters to 20 millimeters (e.g., 15 millimeters) and an example width (e.g., diameter) of the coil 124 of FIG. 2B can be in the range of 2 millimeters to 6 millimeters (e.g., 3 millimeters to 4 millimeters) in the plane substantially perpendicular to the center axis 128. While FIGS. 2A-2B schematically illustrates coils 124 with substantially circular shapes in a plane substantially perpendicular to the center axis 128, other shapes are also compatible with certain implementations described herein (e.g., oval, rectangular, square, polygonal, symmetric, asymmetric, regular, irregular).

Figure 3A:
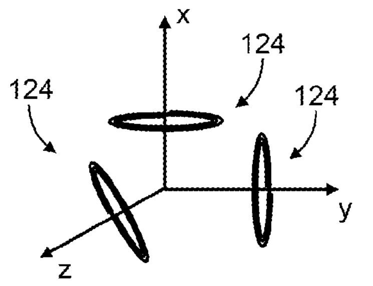
FIGS. 3A-3B schematically illustrate example orientations of the coils of FIG. 2A relative to one another in accordance with certain implementations described herein.
Figure 3B:
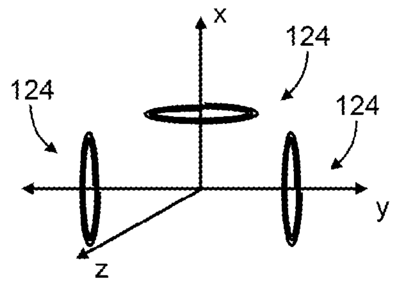
Figure 3C:
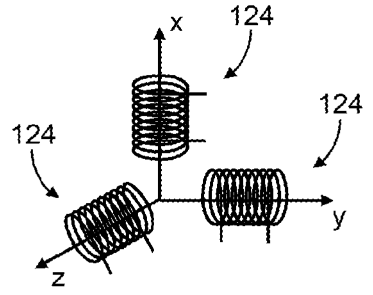
FIGS. 3C-3D schematically illustrate example orientations of the coils of FIG. 2B relative to one another in accordance with certain implementations described herein.
Figure 3D:
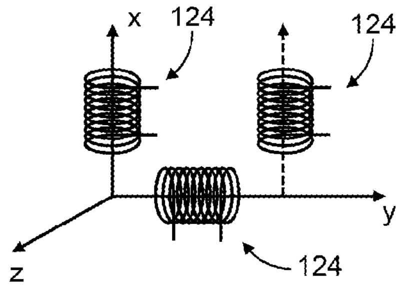

FIGS. 3A-3B schematically illustrate example orientations of the coils 124 of FIG. 2A relative to one another and FIGS. 3C-3D schematically illustrate example orientations of the coils 124 of FIG. 2B relative to one another in accordance with certain implementations described herein. As shown in FIGS. 3A and 3C, in certain implementations, the center axes 128 of the coils 124 are substantially perpendicular to one another. As shown in FIGS. 3B and 3D, the center axes 128 of at least two coils 124 of the plurality of coils 124 are substantially perpendicular to one another (e.g., the center axes 128 of two coils 124 are substantially parallel to one another and the center axis 128 of another coil 124 is substantially perpendicular to the center axes 128 of the two coils 124). Other orientations of the coils 124 are also compatible with certain implementations described herein (e.g., acute angles between two or more of the center axes 128).

Figure 4:
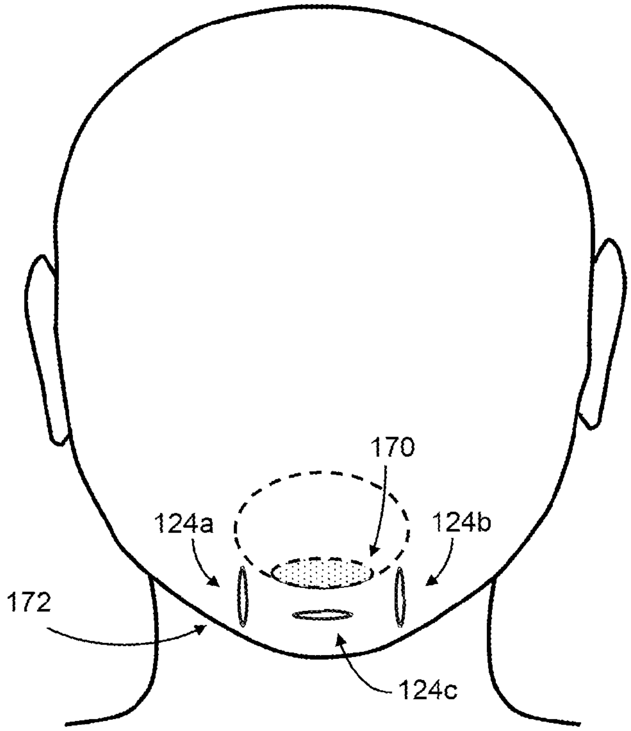
FIG. 4 schematically illustrates an example arrangement of the plurality of coils implanted in a region in proximity to the tongue of the recipient in accordance with certain implementations described herein.

FIG. 4 schematically illustrates an example arrangement of the plurality of coils 124 implanted in a region around (e.g., in proximity to) the tongue 170 of the recipient in accordance with certain implementations described herein. FIG. 4 shows the plurality of coils 124 implanted within a lower jaw region 172 of the recipient's body, with a first coil *124a* at a first side relative to the tongue 170, a second coil *124b* at a second side relative to the tongue 170, the second side opposite to the first side and the center axis 128 of the second coil *124b* substantially parallel to the center axis 128 of the first coil *124a*, and a third coil *124c* implanted below the tongue 170 with the center axis 128 of the third coil *124c* substantially perpendicular to the center axis 128 of the first coil 124*a* and/or the second coil 124*b*. In certain implementations in which the coils 124 are within the same housing 140 as are the stimulation electrodes 114 of the first circuitry 110, the coils 124 are implanted at locations compatible with the stimulation electrodes 114 providing stimulation signals 112 to predetermined portions of the tongue 170 and/or of the hypoglossal nerve.

Various other orientations and/or locations of the coils 124 are also compatible with certain implementations described herein. For example, certain other implementations have only two coils 124, include at least one coil 124 implanted within an upper jaw region of the recipient's body and/or within a neck region of the recipient's body, and/or two or more coils 124 implanted at the same side relative to the tongue 170. For another example, the coils 124 are implanted at locations that are spaced from the locations of the stimulation electrodes 114. In certain implementations in which the external power source 130 comprises a pillow with a plurality of power transmitting coils external to the recipient's body, as described more fully herein, the coils 124 are implanted with orientations and/or positions such that the coils 124 receive a predetermined amount of electrical power from the external power source 130 for a range of positions of the recipient's head relative to the power transmitting coils of the pillow.

The control circuitry 150 of certain implementations comprises processor circuitry (e.g., one or more digital signal processors (DSPs), one or more microcontroller cores, one or more application-specific integrated circuits (ASICs), firmware, software, etc.) configured to provide at least a portion 123 of the electrical power 122 received by the coils 124 to the first circuitry 110 (e.g., to the at least one stimulation electrode 114). In certain implementations, the control circuitry 150 of certain implementations further comprises at least one non-transitory memory device (e.g., random-access memory (RAM) integrated circuit; flash memory) configured to store information to be accessed by the control circuitry 150 for controlling operation of the first circuitry 110 (e.g., generating the stimulation control signals) and/or for controlling operation of the second circuitry 120. In certain implementations, at least a portion of the control circuitry 150 is integral with the first circuitry 110 and/or the second circuitry 120, while in certain other implementations, the control circuitry 150 is separate from both the first circuitry 110 and the second circuitry 120 but operationally coupled to the first circuitry 110 and/or the second circuitry 120.

In certain implementations, a first portion 152 of the control circuitry 150 (e.g., an electrode driver; a portion of the first circuitry 110) is configured to transmit the stimulation control signals to the at least one stimulation element 114, the stimulation control signals indicative of a stimulation signal profile to be applied by the first circuitry 110 to the at least one tongue 170 and/or to the hypoglossal nerve. For example, the first portion 152 of the control circuitry 150 can be configured to provide the stimulation control signals to the first circuitry 110 during the sleep session and the stimulation signal profile can be configured to reduce the muscle fatigue of the at least one tongue 170 during the sleep session. In certain implementations, the first portion 152 of the control circuitry 150 can be configured to generate the stimulation control signals in response at least in part to information from sensor circuitry (not shown) of the apparatus 100. The sensor circuitry can be configured to generate information (e.g., sensor signals) indicative of a condition (e.g., muscle fatigue) of the tongue 170 during the sleep session. For example, the sensor circuitry can comprise an electromyogram (EMG) sensor configured to be positioned externally to the recipient's body (e.g., on the recipient's chin) or implanted on or within the recipient's body (e.g., at a sublingual location) or an evoked compound action potential (ECAP) sensor configured to monitor the response of the hypoglossal nerve to stimulation.

In certain implementations, a second portion 154 of the control circuitry 150 (e.g., a portion of the second circuitry 120) is configured to control and/or modify the electrical power 122 received from the plurality of coils 124. For example, the second portion 154 of the control circuitry 150 can comprise at least one rectifier 156 configured to convert at least a portion 123 of AC electrical power 122 received by the plurality of coils 124 into DC electrical power. The second portion 154 of the control circuitry 150 can further comprise coil selection circuitry 158 configured to determine which coil 124 of the plurality of coils 124 is currently receiving more AC electrical power than are the other coils 124 of the plurality of coils 124 and to provide the AC electrical power from the coil 124 to the at least one rectifier 156. Because each of the coils 124 will have a different position and/or orientation relative to the external power source 130, each of the coils 124 will intercept a different portion of the time-varying magnetic flux generated by the external power source 130 thereby receiving a different amount of electrical power. Furthermore, the amount of magnetic flux intercepted by each coil 124 will change with changes of the orientation and/or position of the recipient's body relative to the external power source 130 (e.g., changes of the orientation and/or position of the portion of the recipient's body in which the coils 124 are implanted) causing the amount of electrical power received by the various coils 124 to change (e.g., over the course of the sleep session). The coil selection circuitry 158 of certain implementations is configured to monitor the amount of electrical power being received by each of the coils 124 in real-time and to transmit the received electrical power received by the coil 124 receiving the largest amount of electrical power in real-time to the at least one rectifier 156.

In certain implementations, as schematically illustrated by FIGS. 1C-1D, the apparatus 100 further comprises power storage circuitry 180 (e.g., at least one rechargeable battery and/or capacitor, such as a super capacitor or tank capacitor) configured to receive and store at least a portion of the power 122 received by the plurality of coils 124 and to distribute the stored power to the various other implanted components (e.g., the first circuitry 110; the control circuitry 150) as needed. For example, the second portion 154 of the control circuitry 150 can be further configured to selectively provide the DC electrical power from the at least one rectifier 156 to the first circuitry 110 and/or to the power storage circuitry 180 which is configured to store the DC electrical power. The control circuitry 150 can be configured to selectively direct stored DC electrical power from the power storage circuitry 180 to the first circuitry 110. The power storage circuitry 180 can be within the portion of the at least one housing 140 that contains the control circuitry 150, as schematically illustrated by FIGS. 1C-1D or can be hermetically sealed within a separate biocompatible housing.

In certain implementations, the power source 130 is external to the recipient's body (denoted in FIGS. 1A-1B as being above the dashed line) (e.g., positioned on an opposite side of the recipient's skin from the implantable second housing 140*b*). The power source 130 comprises at least one power transmitting coil 132 (e.g., RF transmitting coil) external to the recipient's body and configured to generate a time-varying magnetic flux that extends through at least one coil 124 of the plurality of coils 124. For example, the at least one power transmitting coil 132 can comprise at least one turn or loop (e.g., multiple turns or loops) of electrically insulated single-strand or multi-strand wire (e.g., platinum or gold). The at least one coil 124 of the apparatus 100 is configured to respond to the time-varying magnetic flux from the at least one power transmitting coil 132 by generating a time-varying electrical current, thereby wirelessly transferring electrical power (e.g., transcutaneously) from the power source 130 to the apparatus 100. For example, the at least one power transmitting coil 132 can have a resonant frequency in a range of 4 MHz to 10 MHz (e.g., 6.78 MHz) and the time-varying electrical current can have at least one frequency in a range of 200 kHz to 40 MHz (e.g., 20 MHz to 30 MHz; RF) and can be configured to be tuned to provide a sufficiently high Q factor with the plurality of coils 124 of the apparatus 100 for efficient wireless transfer of electrical power from the power source 130 to the apparatus 100 during operation of the power source 130.

Figure 5A:
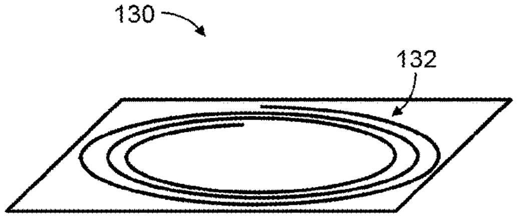
FIGS. 5A-5C schematically illustrate various example power sources in accordance with certain implementations described herein.
Figure 5B:
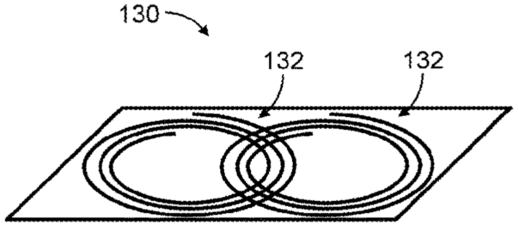
Figure 5C:
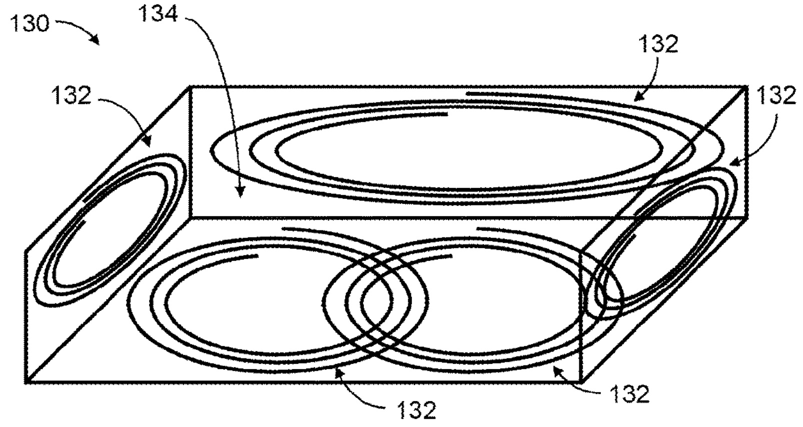

FIGS. 5A-5C schematically illustrate various example power sources 130 in accordance with certain implementations described herein. As schematically illustrated by FIG. 5A, the power source 130 can comprise a single power transmitting coil 132 that is substantially planar. As schematically illustrated by FIG. 5B, the power source 130 can comprise a plurality of power transmitting coils 132 (e.g., substantially planar coils that are substantially parallel or coplanar with one another). Two or more of the power transmitting coils 132 can be positioned to overlap one another, as shown in FIG. 5B, or can be positioned to not overlap one another. As schematically illustrated by FIG. 5C, the power source 130 can comprise a plurality of power transmitting coils 132 (e.g., substantially planar coils). At least some of the coils 132 can be substantially parallel or coplanar with one another, and at least some of the coils 132 can be substantially perpendicular to one or more other coils 132 (e.g., in three orthogonal orientations). As shown in FIG. 5C, the coils 132 of certain implementations can be positioned around a region 134 (e.g., along two or more sides of the region 134) in which the coils 124 of the apparatus 100 are to be placed during power transfer from the power source 130 to the apparatus 100. In certain implementations, the power source 130 can be integral with a pillow or other cushion for the recipient to rest the recipient's head during a sleep session, and the power source 130 can be activated to transfer power to the apparatus 100 implanted on or within the recipient's head during the sleep session. Example power sources 130 compatible with certain implementations described herein are disclosed by U.S. Pat. No. 10,530,177.

In certain implementations, the apparatus 100 is powered directly by the electrical power received from the power source 130 during the wireless transfer of electrical power. In certain other implementations, the apparatus 100 stores at least a portion of the received power in the power storage circuitry 180 and the apparatus 100 is powered by stored electrical power retrieved from the power storage circuitry 180 (e.g., in time periods during which the implanted coils 124 have insufficient coupling with the power source 130; the recipient's head rolls off the pillow of the power source 130 during the sleep session). In certain implementations, the power storage circuitry 180 can comprise a supercapacitor configured to store electrical power in the form of electrical charge from the conversion of the time-varying magnetic field) and to release the stored electrical power in the form of electrical charge to the at least one stimulation electrode 114 once a predefined charge threshold is reached. To avoid unwanted stimulation, the wireless power transfer from the power source 130 to the apparatus can be controlled remotely by an external device (e.g., smart phone; smart tablet; smart watch; other remote device operated by the recipient) or the wireless power transfer can be active only when the recipient's head is in a horizontal position (e.g., as detected by at least one accelerometer of the apparatus 100).

In certain implementations, the apparatus 100 further comprises communication circuitry configured to receive signals from and/or transmit signals to a device external to the recipient's body (e.g., the power source 130; smart phone; smart tablet; smart watch; other remote device operated by the recipient). For example, the communication circuitry can comprise at least one signal transceiver having at least one antenna (e.g., wire coil comprising multiple turns of electrically insulated single-strand or multi-strand platinum or gold wire) that is part of an inductive radio frequency (RF) communication link and is configured to receive control information wirelessly transmitted from the external device and/or to wirelessly transmit status information to the external device. In certain implementations, the at least one antenna of the communication circuitry can comprise one or more coils 124 of the plurality of coils 124, while in certain other implementations, the at least one antenna is separate from the plurality of coils 124 configured to receive electrical power from the power source 130.

Figure 6:
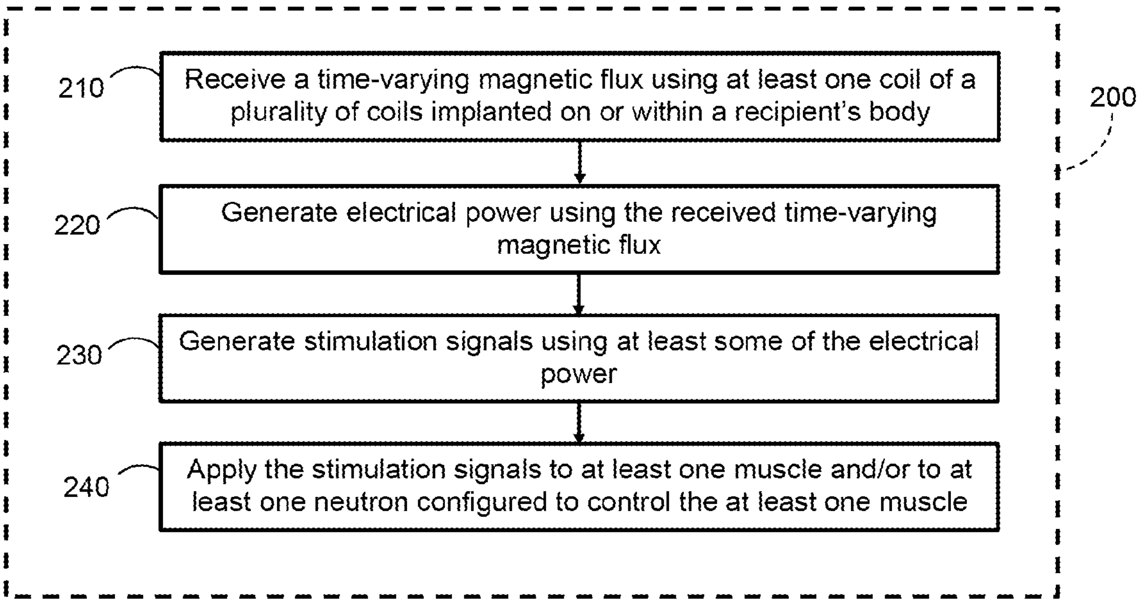
FIG. 6 is a flow diagram of an example method in accordance with certain implementations described herein.

FIG. 6 is a flow diagram of an example method 200 in accordance with certain implementations described herein. In an operational block 210, the method 200 comprises receiving a time-varying magnetic flux using at least one coil 124 of a plurality of coils 124 implanted on or within a recipient's body. The coils 124 have different orientations and/or positions relative to one another. In an operational block 220, the method 200 further comprises generating electrical power using the received time-varying magnetic flux. In an operational block 230, the method 200 further comprises generating stimulation signals using at least some of the electrical power. In an operational block 240, the method 200 further comprises applying the stimulation signals to at least one muscle of the recipient's body and/or to at least one neuron configured to control the at least one muscle. For example, the at least one muscle can comprise at least one tongue muscle and the stimulation signals can be applied during a sleep session of the recipient to treat obstructive sleep apnea. In certain implementations, the method 200 further comprises evaluating which coil 124 of the plurality of coils 124 is receiving a larger fraction of the time-varying magnetic flux than are other coils 124 of the plurality of coils 124 and using the electrical power generated by the coil 124 receiving the larger fraction of the time-varying magnetic flux to generate the stimulation signals.

Although commonly used terms are used to describe the systems and methods of certain implementations for ease of understanding, these terms are used herein to have their broadest reasonable interpretations. Although various aspects of the disclosure are described with regard to illustrative examples and implementations, the disclosed examples and implementations should not be construed as limiting. Conditional language, such as, among others, "can," "could," "might," or "may," unless specifically stated otherwise, or otherwise understood within the context as used, is generally intended to convey that certain implementations include, while other implementations do not include, certain features, elements and/or steps. Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

It is to be appreciated that the implementations disclosed herein are not mutually exclusive and may be combined with one another in various arrangements. In addition, although the disclosed methods and apparatuses have largely been described in the context of conventional cochlear implants, various implementations described herein can be incorporated in a variety of other suitable devices, methods, and contexts. More generally, as can be appreciated, certain implementations described herein can be used in a variety of implantable medical device contexts that can benefit from having at least a portion of the received power available for use by the implanted device during time periods in which the at least one power storage device of the implanted device unable to provide electrical power for operation of the implantable medical device.

Language of degree, as used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within ±10% of, within ±5% of, within ±2% of, within ±1% of, or within ±0.1% of the stated amount. As another example, the terms "generally parallel" and "substantially parallel" refer to a value, amount, or characteristic that departs from exactly parallel by ±10 degrees, by ±5 degrees, by ±2 degrees, by ±1 degree, or by ±0.1 degree, and the terms "generally perpendicular" and "substantially perpendicular" refer to a value, amount, or characteristic that departs from exactly perpendicular by ±10 degrees, by ±5 degrees, by ±2 degrees, by ±1 degree, or by ±0.1 degree. The ranges disclosed herein also encompass any and all overlap, sub-ranges, and combinations thereof. Language such as "up to," "at least," "greater than," less than," "between," and the like includes the number recited. As used herein, the meaning of "a," "an," and "said" includes plural reference unless the context clearly dictates otherwise. Also, as used in the description herein, the meaning of "in" includes "into" and "on," unless the context clearly dictates otherwise.

Spatially relative terms, such as "above," "below," "over," "under," "upper," and "lower" and the like, may be used herein for ease of description to describe one element or feature's relationship to another as illustrated in the figures. It will be understood that the spatially relative terms are intended to encompass different orientations of the components in use or operation in addition to the orientation depicted in the figures. For example, if a device in the figures is inverted, elements described as "above" or "over" other elements or features would then be oriented "below" or "beneath" the other elements or features. Thus, the exemplary term "above" can encompass both an orientation of above and below. The device may be otherwise oriented (e.g., rotated 90 degrees or at other orientations) and the spatially relative descriptors used herein interpreted accordingly. Similarly, the terms "upwardly," "downwardly," "vertical," "horizontal," and the like are used herein for the purpose of explanation only unless specifically indicated otherwise.

While the methods and systems are discussed herein in terms of elements labeled by ordinal adjectives (e.g., first, second, etc.), the ordinal adjectives are used merely as labels to distinguish one element from another (e.g., one signal from another or one circuit from one another), and the ordinal adjective is not used to denote an order of these elements or of their use.

The invention described and claimed herein is not to be limited in scope by the specific example implementations herein disclosed, since these implementations are intended as illustrations, and not limitations, of several aspects of the invention. Any equivalent implementations are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example implementations disclosed herein, but should be defined only in accordance with the claims and their equivalents.

What is claimed is:

1. An apparatus comprising:

first circuitry configured to be implanted on or within a recipient's body, the first circuitry configured to apply stimulation signals to at least one muscle of a recipient and/or to at least one neuron configured to control the at least one muscle; and second circuitry configured to be implanted on or within the recipient's body, the second circuitry configured to wirelessly receive electrical power from a power source external to the recipient's body and to provide at least a portion of the received electrical power to the first circuitry, the second circuitry comprising:

a plurality of coils, each coil of the plurality of coils comprising at least one electrically conductive conduit encircling a center axis of the coil, the coils configured to be implanted on or within the recipient's body with different orientations and/or positions relative to one another;

at least one rectifier configured to convert at least a portion of AC electrical power received by the plurality of coils into DC electrical power; and coil selection circuitry configured to determine which coil of the plurality of coils is currently receiving more AC electrical power than are the other coils of the plurality of coils and to provide the AC electrical power from the coil to the at least one rectifier.

2. The apparatus of claim 1, wherein the first circuitry comprises at least one stimulation electrode configured to be implanted on or within the recipient's body and to apply the stimulation signals to a portion of the tongue of the recipient and/or to a portion of a hypoglossal nerve of the recipient during a sleep session of the recipient.

3. The apparatus of claim 2, wherein the at least one stimulation electrode comprises a cuff electrode and/or a surface electrode, the at least one stimulation electrode configured to apply an electrical voltage and/or current to the portion of the hypoglossal nerve.

4. The apparatus of claim 1, wherein the coils are configured to be implanted within a lower jaw region, an upper jaw region, and/or a neck region of the recipient's body.

5. The apparatus of claim 1, further comprising a plurality of power transmitting coils external to the recipient's body, the plurality of power transmitting coils configured to generate a time-varying magnetic flux that extends through at least one coil of the plurality of coils, the at least one coil configured to respond to the time-varying magnetic flux by generating a time-varying electrical current.

6. The apparatus of claim 1, wherein the center axes of at least two coils of the plurality of coils are substantially perpendicular to one another.

7. The apparatus of claim 1, wherein at least one coil of the plurality of coils is substantially planar and perpendicular to the center axis of the coil.

8. The apparatus of claim 1, wherein at least one coil of the plurality of coils is substantially cylindrical with a longitudinal axis that is parallel to and/or coincident with the center axis of the coil.

9. The apparatus of claim 1, wherein the second circuitry is further configured to selectively provide the DC electrical power to the first circuitry and/or to power storage circuitry configured to store the DC electrical power and to provide stored DC electrical power to the first circuitry.

10. The apparatus of claim 9, wherein the power storage circuitry comprises a tank capacitor.

11. A method comprising:

receiving a time-varying magnetic flux using at least one coil of a plurality of coils implanted on or within a recipient's body, the coils having different orientations and/or positions relative to one another;

evaluating which coil of the plurality of coils is receiving a larger fraction of the time-varying magnetic flux than are other coils of the plurality of coils;

generating electrical power using the time-varying magnetic flux received by the coil;

generating stimulation signals using at least some of the electrical power generated by the coil; and applying the stimulation signals to at least one muscle of the recipient's body and/or to at least one neuron configured to control the at least one muscle.

12. The method of claim 11, wherein the at least one muscle comprises at least one tongue muscle, said applying the stimulation signals performed during a sleep session of the recipient to treat obstructive sleep apnea.

13. The method of claim 11, wherein each coil of the plurality of coils comprises at least one electrically conductive conduit encircling a center axis of the coil.

14. An apparatus comprising:

at least one implantable electrode configured to apply stimulation signals to at least one muscle of a recipient and/or to at least one neuron configured to control the at least one muscle;

a plurality of implantable RF coils having different orientations and/or positions relative to one another, the plurality of implantable RF coils configured to wirelessly receive electrical power from an external power source; and processor circuitry configured to provide at least a portion of the electrical power received by the plurality of implantable RF coils to the at least one implantable electrode and further configured to monitor which RF coil of the plurality of implantable RF coils is receiving more electrical power than are the other RF coils of the plurality of implantable RF coils, to rectify the electrical power from the RF coil, and to provide the rectified electrical power to the at least one implantable electrode.

15. The apparatus of claim 14, further comprising at least one capacitor configured to store at least a portion of the received electrical power, the processor circuitry further configured to selectively direct stored electrical power from the at least one capacitor to the at least one implantable electrode.

16. The apparatus of claim 14, wherein the at least one muscle comprises a portion of the tongue of the recipient and the at least one neuron comprises a portion of a hypoglossal nerve of the recipient.

17. The apparatus of claim 14, wherein at least one of the RF coils is substantially planar or substantially cylindrical and has a center axis that is substantially perpendicular to a center axis of at least one other of the RF coils.

18. The apparatus of claim 14, wherein changes of the orientation and/or position of the recipient's body relative to the external power source change the electrical power received by each RF coil of the plurality of implantable RF coils and the processor circuitry is configured to monitor, in real-time, the amount of electrical power being received by each of the RF coils and to change, in real-time, which RF coil provides the electrical power that is rectified and provided to the at least one implantable electrode.

* * * * *